United States Patent
Guo

(10) Patent No.: US 10,599,771 B2
(45) Date of Patent: Mar. 24, 2020

(54) NEGATION SCOPE ANALYSIS FOR NEGATION DETECTION

(71) Applicant: INTERNATIONAL BUSINESS MACHINES CORPORATION, Armonk, NY (US)

(72) Inventor: Yufan Guo, San Jose, CA (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 0 days.

(21) Appl. No.: 15/483,750

(22) Filed: Apr. 10, 2017

(65) Prior Publication Data

US 2018/0293227 A1  Oct. 11, 2018

(51) Int. Cl.
| | | |
|---|---|---|
| G06F 17/27 | (2006.01) | |
| G06F 16/33 | (2019.01) | |
| G16H 50/20 | (2018.01) | |
| G16H 10/60 | (2018.01) | |
| G16H 15/00 | (2018.01) | |

(52) U.S. Cl.
CPC ...... G06F 17/2785 (2013.01); G06F 16/3344 (2019.01); G06F 17/2705 (2013.01); G06F 17/2775 (2013.01); G06F 17/2795 (2013.01); G16H 10/60 (2018.01); G16H 15/00 (2018.01); G16H 50/20 (2018.01)

(58) Field of Classification Search
CPC .............. G06F 17/2785; G06F 16/3344; G06F 17/2705; G06F 17/2775; G06F 17/2795; G16H 10/60; G16H 15/00; G16H 50/20
See application file for complete search history.

(56) References Cited

U.S. PATENT DOCUMENTS

| | | | | |
|---|---|---|---|---|
| 5,905,982 A | * | 5/1999 | Carey | G06F 16/289 707/694 |
| 6,622,140 B1 | * | 9/2003 | Kantrowitz | G06F 17/30707 |
| 9,213,687 B2 | * | 12/2015 | Au | G06F 17/274 |
| 9,633,007 B1 | * | 4/2017 | Brun | G06F 17/2785 |
| 9,715,488 B2 | * | 7/2017 | Bruno | G06F 17/2705 |
| 2002/0133331 A1 | * | 9/2002 | Kharrat | G06F 17/271 704/9 |
| 2007/0203709 A1 | * | 8/2007 | Yasutaka | G10L 15/22 704/275 |

(Continued)

OTHER PUBLICATIONS

Vincze et al., "The BioScope corpus: biomedical texts annotated for uncertainty, negation and their scopes", Natural Language Processing Biomedicine (BioNLP) ACL Workshop 2008. (Year: 2008).*
Sohn et al., "Dependency Parase-based Negation Detection in Clinical Narratives", AMIA Jt Summits Transl Sci Proc. 2012; 2012: 1-8. (Year: 2012).*

(Continued)

*Primary Examiner* — Fariba Sirjani
(74) *Attorney, Agent, or Firm* — Erik Huestis; Stephen Kenny; Foley Hoag

(57) ABSTRACT

Negation scope analysis for negation detection is provided. In various embodiments, a phrase is read from a report collection. The phrase is searched for at least one of a predetermined set of negation keywords. A dependency parse tree is generated of the phrase. The dependency parse tree is traversed starting with the at least one of the predetermined set of negation keywords. Based on the traversal, a plurality of words of the phrase are determined that are spanned by the at least one of the predetermined set of negation keywords.

14 Claims, 6 Drawing Sheets

(56) References Cited

U.S. PATENT DOCUMENTS

| | | | | |
|---|---|---|---|---|
| 2008/0249764 | A1* | 10/2008 | Huang | G06F 17/2785 704/9 |
| 2009/0077069 | A1* | 3/2009 | Polanyi | G06F 17/3061 |
| 2011/0099133 | A1* | 4/2011 | Chang | G06F 17/30707 706/12 |
| 2012/0101808 | A1* | 4/2012 | Duong-Van | G06F 17/2785 704/9 |
| 2012/0166180 | A1* | 6/2012 | Au | G06F 17/27 704/9 |
| 2012/0197903 | A1* | 8/2012 | Lu | G06F 17/2785 707/748 |
| 2013/0103386 | A1* | 4/2013 | Zhang | G06F 17/2785 704/9 |
| 2013/0103667 | A1* | 4/2013 | Minh | G06F 17/30864 707/709 |
| 2013/0332460 | A1* | 12/2013 | Pappas | G06F 17/30705 707/740 |
| 2014/0019118 | A1* | 1/2014 | Tromp | G06F 17/274 704/9 |
| 2014/0067370 | A1* | 3/2014 | Brun | G06F 17/271 704/9 |
| 2014/0229445 | A1* | 8/2014 | Carter | H04L 51/32 707/679 |
| 2014/0280179 | A1* | 9/2014 | Coleman | G06F 17/30643 707/740 |
| 2015/0120788 | A1* | 4/2015 | Brun | G06F 17/30312 707/812 |
| 2015/0149461 | A1* | 5/2015 | Aguilar Lemarroy | G06F 17/30705 707/737 |
| 2015/0193523 | A1* | 7/2015 | Cox | G06N 5/025 707/737 |
| 2015/0261744 | A1* | 9/2015 | Suenbuel | G06F 17/271 704/9 |
| 2016/0098389 | A1* | 4/2016 | Bruno | G06F 17/2705 704/9 |
| 2017/0004184 | A1* | 1/2017 | Jain | G06F 17/2735 |

OTHER PUBLICATIONS

Mutalik et al., "Use of General-purpose Negation Detection to Augment Concept Indexing of Medical Documents: A Quantitative Study Using the UMLS", Journal of the American Medical Informatics Association, vol. 8, Issue 6, Nov. 1, 2001. (Year: 2001).*

Meystre et al., "Comparing Natural Language Processing Tools to Extract Medical Problems from Narrative Text", AMIA Annu Symp Proc. 2005; 2005: 525-529. (Year: 2005).*

Leroy et al., "Genescene: An Ontology-Enhanced Integration of Linguistic and Co-Occurrence Based Relations in Biomedical Texts", vol. 56, issue 5, Special Issue: Bioinformatics, Mar. 2005, pp. 457-468. (Year: 2005).*

Mehrabi, S.; Krishnan, A.; Sohn, S.; Roch, A. M.; Schmidt, H.; Kesterson, J.; Beesley, C.; Dexter, P.; Schmidt, C. M.; Liu, H.; et al. 2015. Deepen: A negation detection system for clinical text incorporating dependency relation into NegEx.*

Sohn, S.;Wu, S.; and Chute, C. G. 2012. Dependency parser-based negation detection in clinical narratives. In AMIA Jt Summits Transl Sci Proc, 1-8.*

Yufan Guo, Deepika Kakrania, Tyler Baldwin, Tanveer F Syeda-Mahmood. AAAI. 2017. Efficient clinical concept extraction in electronic medical records. In; pp. 5089-5090.*

Chapman, W. W.; Bridewell, W.; Hanbury, P.; Cooper, G. F.; and Buchanna, B. G. 2001. A simple algorithm for identifying negated findings and diseases in discharge summaries. J Biomed Inform 34(5):301-310.*

Shashank Agarwal et Al.,Biomedical Negation Scope Detection with Conditional Random Fields, J Am Med Inform Assoc, Nov.-Dec. 2010, pp. 696-701, vol. 17, Issue 6, NCBI.

Councill et Al.,What's Great and What's Not:Learning to Classify the Scope of Negation for Improved Sentiment Analysis,Proc. workshop on Negation and Speculltion NLP,Jul. 2010.

Tanushi et Al.,Negation Scope Delimitation in Clinical Text Using Three Approaches:NegEx, PyConTextNLP and Syn-Neg;NODALIDA,May 22-24, 2013,Norway:Linköping Univers; Stp.lingfi.

* cited by examiner

NEGATION SCOPE ANALYSIS FOR NEGATION DETECTION

BACKGROUND

Embodiments of the present disclosure relate to negation detection, and more specifically, to negation scope analysis for negation detection.

BRIEF SUMMARY

According to embodiments of the present disclosure, methods of and computer program products for negation detection are provided. A phrase is read from a report collection. The phrase is searched for at least one of a predetermined set of negation keywords. A dependency parse tree is generated of the phrase. The dependency parse tree is traversed starting with the at least one of the predetermined set of negation keywords. Based on the traversal, a plurality of words of the phrase are determined that are spanned by the at least one of the predetermined set of negation keywords.

DETAILED DESCRIPTION

Figure 1:
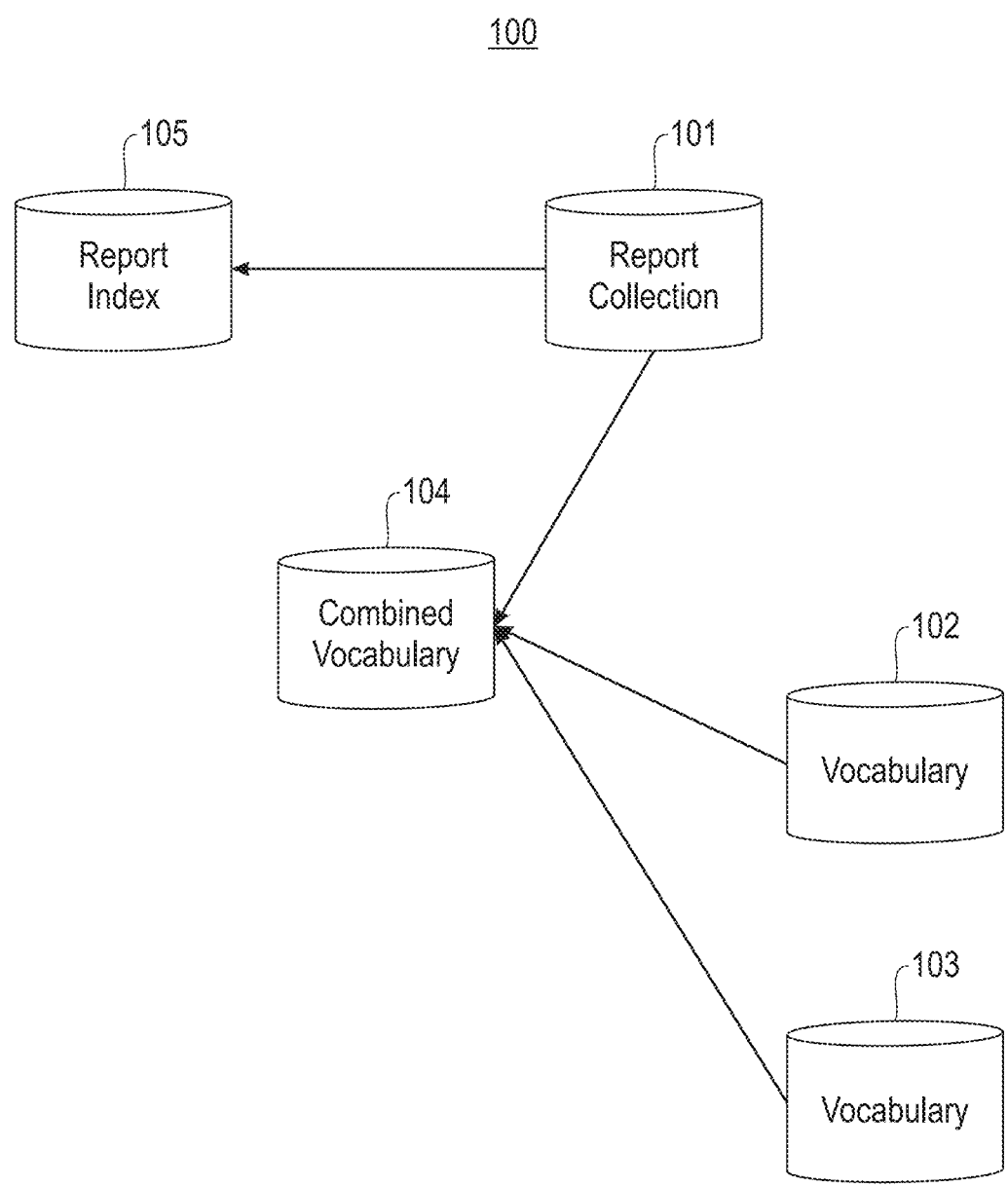
FIG. 1 illustrates a system for concept extraction according to embodiments of the present disclosure.

The present disclosure provides for the detection of clinical concepts in very large clinical report collections. To enable scalable concept extraction of high sensitivity and specificity, various enhancements are provided. A vocabulary of over 5 million concept terms is formed by combining existing standard vocabularies with concept phrases mined from clinical reports. Concept vocabulary phrases are identified within reports via a string matching algorithm described herein, which tolerates higher semantically consistent variation than vocabulary-driven concept extraction methods. The detected phrases are analyzed for negation using a negation detection algorithm such as provided herein. An efficient search algorithm is provided based on indexing of the report collections to allow fast and accurate identification of vocabulary phrases in report sentences without needing detailed search.

One important source of clinical information in patient health records is the clinical report, which documents findings from radiology, cardiology, pathology, labs, etc. Structured information recorded in EMR systems does not capture all the symptoms, diagnoses, medications, or measurements found in reports. Automatic extraction of these concepts is therefore useful in not only forming a complete longitudinal health record of the patient from a clinical care standpoint, but in recovering missing codes for billing, and finding more accurate clinical cohorts for clinical trials. Inset 1 provides an exemplary section of a report from a cardiac echo study, illustrating disease and measurement findings in the domain of cardiology. These documents summarize the findings in many diagnostic settings and record important measurements taken from devices under various tests. Mining such reports can reveal important disease information not captured in structured records as well as help study the correlation of diagnosis with their descriptions and measurements. In particular, similar disease labels can be inferred for patients with similar diagnosis reports to help in clinical decision support.

---
Inset 1
---
Mitral Valve: There is marked mitral annular calcification present which causes restriction of mitral inflow. The mitral valve leaflets are calcified and restricted. Severe mitral regurgitation is present. There is systolic flow reversal in the pulmonary vein.

---

An electronic health record (EHR), or electronic medical record (EMR), may refer to the systematized collection of patient and population electronically-stored health information in a digital format. These records can be shared across different health care settings and may extend beyond the information available in a PACS discussed above. Records may be shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information.

EHR systems may be designed to store data and capture the state of a patient across time. In this way, the need to track down a patient's previous paper medical records is eliminated. In addition, an EHR system may assist in ensuring that data is accurate and legible. It may reduce risk of data replication as the data is centralized. Due to the digital information being searchable, EMRs may be more effective when extracting medical data for the examination of possible trends and long term changes in a patient. Population-based studies of medical records may also be facilitated by the widespread adoption of EHRs and EMRs.

Health Level-7 or HL7 refers to a set of international standards for transfer of clinical and administrative data between software applications used by various healthcare providers. These standards focus on the application layer, which is layer 7 in the OSI model. Hospitals and other healthcare provider organizations may have many different computer systems used for everything from billing records to patient tracking. Ideally, all of these systems may communicate with each other when they receive new information or when they wish to retrieve information, but adoption of such approaches is not widespread. These data standards are meant to allow healthcare organizations to easily share clinical information. This ability to exchange information may help to minimize variability in medical care and the tendency for medical care to be geographically isolated.

In various systems, connections between a PACS, Electronic Medical Record (EMR), Hospital Information System (HIS), Radiology Information System (RIS), or report repository are provided. In this way, records and reports form the EMR may be ingested for analysis. For example, in addition to ingesting and storing HL7 orders and results messages, ADT messages may be used, or an EMR, RIS, or report repository may be queried directly via product specific mechanisms. Such mechanisms include Fast Health Interoperability Resources (FHIR) for relevant clinical information. Clinical data may also be obtained via receipt of various HL7 CDA documents such as a Continuity of Care Document (CCD). Various additional proprietary or site-customized query methods may also be employed in addition to the standard methods.

One approach to finding clinical concepts in reports is through the use of a vocabulary. The vocabulary may be assembled manually by taking clinical terminologies such as conformant to the names used in the clinical dictionaries, and handling a small amount of lexical variations is usually insufficient, leading to considerable loss in recall. Again, as can be seen from Table 1, a better modeling of the word variations in dictated reports is needed in order to robustly match vocabulary phrases to their occurrences in sentences. Such a matching may be inexact, account for missing or spurious phrases, or may not match entire words, while still ensuring that the semantic meaning of the vocabulary phrase is captured.

TABLE 1

| Prefix strings | Vocabulary phrase | Matching sentence in a textual report |
| --- | --- | --- |
| Aort:sclero | Aortic sclerosis | Marked aortic sclerosis present with |
| Aort:sten | Aortic stenosis | evidence of stenosis. |
| Frac:clav | Fracture of clavicle | There is a transverse fracture of the mild left clavicle with mild superior angulation of the fracture fragment. |
| Perfor:esop | Perforation of esophagus | A contrast esophagram shows esophageal perforation of the anterior left esophagus at C4-5 with extraluminal contrast seen. |
| Edem:lower:extrem | Edema of lower extremity | EXTREMITIES: Lower extremity trace pitting edema and bilateral lower extremity toe ulceration and onychomycosis, right plantar eschar. |
| Atri:dila | Atrial dilatation | Left Atrium: Left atrial size is mildly dilated. |
| Mass:left:brea | Mass in left breast | new lft breast palp mass found. |
| Abno:finding:lung | Abnormal findings in lungs | abn findings-lung field. |
| Abno:cerv:smear | Abnormal cervical smear | Prior abnormal Pap smear with ASCUS and positive HPV screen |

UMLS and augmenting them with hospital-specific terms such as the Mayo-specific terms that are already curated and available. To find the clinical terms, the reports are parsed and broken into sentences. Noun phrases are selected within a sentence and searched against a dictionary. Negated contexts are separated from positive indications of the concept through the use of a negation vocabulary and regular expression negation patterns. The performance of a concept detection algorithm depends on several factors: the size of the vocabulary; the algorithm used for finding a match including reliable detection of negations; and its scalability in the presence of large documents and large vocabularies. If the vocabularies are manually created, such as those from clinical terminologies, finding their evidence in actual dictated reports becomes difficult as the vocabulary words are rarely used in the same form as in their definitions.

Table 1 shows this problem in the context of disease concepts where the actual dictated sentence in the report appears considerably deviated from the corresponding vocabulary phrase shown in Column 2 of Table 1. If the vocabulary could be augmented with frequently occurring concept-depicting phrases mined from large training collections of actual reports, the concept extraction algorithms could expect to improve their performance.

Various such vocabulary-based approaches provide complex parsing and extraction of semantic tokens in concept search literature paired with a simple matching algorithm. Some such matching algorithms search for exact occurrence of vocabulary phrases as strings within sentences or through simple edit distance metrics. Although some non-lexical variations of the head or modifiers within noun phrases are allowed, the matching is predominantly a lookup operation. The actual usage of clinical terms in reports is hardly Various concept detection algorithms employ methods that linearly search through the report sentences for occurrences of vocabulary phrases. This becomes impractical and such approaches do not scale when large report collections exceeding millions of reports that may be present in large hospital settings need to be analyzed.

The present disclosure addresses the above problems and enables a scalable concept extraction of high sensitivity and specificity in very large document collections of over 10 million reports through various enhancements. In various embodiments, a large knowledge graph is formed of over 5.6 million concept terms by combining over 70 reference vocabularies such as SNOMED CT, ICD9, ICD 10, RadLex, RxNorm, and LOINC and use its concept nodes as vocabulary phrases.

In various embodiments, a string matching algorithm is provided, referred to herein as the longest common subfix algorithm, to find optimal occurrence of vocabulary phrases within sentences in textual reports. The algorithm tolerates much higher semantically consistent variation in the appearance of vocabulary phrases in dictated reports than is currently possible in vocabulary-driven concept extraction. The detected concepts are then tested for negative occurrences using a new negation detection algorithm.

In various embodiments, an efficient search algorithm is provided based on indexing the report collections to allow fast and accurate identification of relevant vocabulary phrases in relevant sentences in reports without needing detailed search. A comparison with alternative concept search algorithms shows the algorithm outperforms these algorithms in precision and recall in addition to scaling to such large collections.

The extraction of clinical concepts from unstructured reports may be referred to as named entity recognition in the clinical domain. Various approaches are possible, ranging from handcrafted rule-based algorithms to using machine learning and pattern inference techniques. This problem may be addressed in the context of inferring diagnostic codes from patient records. In such approaches, simple learning approaches such as k-nearest neighbor or relevance feedback are used to acquire knowledge from already coded training documents. However, clinical concepts may be identified through the use of known vocabularies. For example, candidate phrases may be identified through shallow parsing in reports and mapping these phrases to the UMLS thesaurus. In another example, phrases may be mapped to UMLS semantic types and then to more specific semantic categories such as diagnosis and procedures. Other approaches use a combination of domain vocabulary and findings mentioned in radiology reports to explore assignment of codes.

Concept mapping systems may employ string matching algorithms to do the mapping. Some approaches enrich string features with syntactic information such as parts of speech and phrase tags to map entire records to codes. For example, substrings of stemmed input text may be matched to stemmed concepts in a thesaurus respecting the order of words. Some approaches allow the permutation of word order in the input text. However, the permutations of word order can alter the meaning, particularly when more than one disease name is mentioned in a textual phrase and the relationship is disturbed by permuting the order. Word stemming to model the word variations is also possible. For example, diagnosis labeling may be done by extracting noun phrases and doing an exact match lookup of the phrase against a UMLS concept. If no match is found, stemming and normalization is used to truncate the string before lookup again.

Some approaches may employ a negation detection algorithm to also spot negative occurrences of diseases or symptoms. Various approaches to negation detection use regular expression patterns seeded by negation phrases that appear before or after a finding. This may be done after the UMLS phrase has already been found in the sentence and the phrase is treated en-block in the pattern. When more than one concept phrase is present in a sentence, the negation may be associated with the wrong phrase.

When the vocabulary words are in the millions, and the number of reports to be analyzed on the scale of 10 million reports or more, performance considerations take on additional importance. With increased vocabulary words and large collections, the precision and recall performance of various algorithms outlined above are severely affected. In addition, automatic extraction processes without efficient indexing mechanisms can take time on order of months if not years. As a result, straightforward clinical concept extraction may be impractical for large electronic health record systems.

The present disclosure addresses the need for scalable concept extraction systems for large vocabularies and large collections of reports using various enhancements including: semi-automatic generation of a large vocabulary by consolidating and cross-linking the UMLS ontologies; an enhanced matching algorithm with extended support of negations; and indexing of large report collections for efficient search.

In various embodiments, methods for semi-automatic generation of clinical vocabularies are provided. In various embodiments, an algorithm is provided for string matching by modeling spoken variations in vocabulary words through prefix matching of 'must have' vocabulary terms. In various embodiments, an enhanced negation detection algorithm is provided that uses lexical and syntactic analysis to determine the span of negations. In various embodiments, indexing methods are provided to enable fast search of collections. An overall algorithm for clinical concept extraction is also provided. In various embodiments, an extended negation finding algorithm is provided that not only spots negative occurrences of disease terms but also rules out terms that indicate that a family member has a problem instead of the patient.

Referring now to FIG. 1, an exemplary system for concept extraction is illustrated according to embodiments of the present disclosure. Collection 101 comprises a plurality of clinical reports. As set out further above, the clinical reports may be accessed through various channels such as HL7. A plurality of external vocabularies 102 . . . 103 are used to generate a combined vocabulary 104. In some embodiments, the clinical report collection 101 is further mined to supplement combined vocabulary 104.

The exemplary vocabulary described herein for clinical concept extraction was derived from two sources, clinical reference dictionaries and learned words from the analysis of a large number of reports.

In this exemplary vocabulary, several categories of clinical concepts were modeled, including diseases, symptoms, medications, exams/procedures, and measurements using the UMLS defined categories. The initial vocabulary was drawn from SNOMED CT, ICD9, MSDRG, and APDRG codes for diseases, SNOMED CT for symptoms, RxNorm for medications, and LOINC for exams and measurements. Of the 393,073 concepts in SNOMED CT 2011 standard, the 146 types of terms in SNOMED CT were analyzed and a subset of these types was used to form the base vocabulary for the five concept types. Additional drug vocabulary was added by taking all of the RxNorm data of over 807,302 drug terms and curating them to remove references to diseases to form a pure drug vocabulary. The unmodified RxNorm drug collection has many terms that either indicate concepts other than drugs (e.g., diseases) or name forms which by themselves are not useful for concept detection (e.g., the term 'blue'). After curation, 200,000 drug names were retained that included brand names, generics as well as chemical names. Similarly, the LOINC data was analyzed and several columns of the LOINC table columns were retained for describing exam names, procedures and measurement names and ranges.

In large collections of reports, the reference vocabulary is often transformed semantically in written documents, with cases of out-of-order words, abbreviations, different word forms, etc. often present. Table 1 (above) provides examples of actual phrases in reports and the corresponding vocabulary words that can be inferred. In order to allow for such variable appearances when matching vocabulary words, the vocabulary set is supplemented by recording the most frequently occurring spoken patterns through mining of large collections of reports. Specifically, in this example, about 12.9 million reports covering about 800,000 patients were obtained from a large hospital system. To extract the most frequent phrases, a subset of 1.2 million reports were used as training documents. This subset comprised over 200 different types of reports including clinical history notes, pathology, transcription, radiology, lab systems, and cardiology reports.

In processing the training documents, the unstructured text was segmented into separate sentences. In addition to using sentence separators, the document layout analysis of the reports was used to separate the reports into sections. Since many of the reports came as part of HL7 messages, section information was often available in the tags in order to allow paragraph and sentence separation. The n-gram phrases were extracted, where n was varied from 1 to 13 within each sentence (assuming a maximum of 13 words to describe a concept such as a disease). The n-gram phrases were generated by sliding a window of size n words consecutively through a sentence so that the set of n-grams were generated in time linear in the number of words per sentence. They were then sorted by frequency and the most commonly occurring phrases were then manually analyzed and retained if they were indicative of the modeled concepts (diseases, symptoms, drugs, etc.) and added to the reference vocabulary. This process was repeated for all concept types resulting in a total vocabulary of 871,450 terms for 5 of the clinical concepts.

As can be seen from Table 1, expecting an exact match to vocabulary phrases by direct string lookup can be unreasonable when applied to large report collections. Even if string matching could be augmented with syntactic information such as parts of speech or phrase tags, or the word order is permuted, false matches or semantically incorrect matches are possible. It is desirable for the vocabulary phrasal matching to be tolerant to the word variant formation based on rules of grammar (English, in this case) for tenses, active or passive voices, singular or plural, while retaining the semantics. Further, the matching should be robust to a few missing words or presence of extra words as illustrated by the examples in Table 1. In addition, it is desirable for many of the words of the vocabulary phrase to find a match in a single sentence in the report.

An algorithm is provided below for inexact matching of vocabulary phrases to phrases within sentences in textual reports that guarantees the largest number of words of the vocabulary phrase are matched to the largest possible extent while still maintaining the word order and allowing missed and spurious words in between. This algorithm is referred to herein as a longest common subfix algorithm.

Given a query vocabulary phrase $S=\langle s_1 s_2 \ldots s_K \rangle$ of K words and a candidate sentence $T=\langle t_1 t_2 \ldots t_N \rangle$ of N words, the longest common subfix is defined as $LCF(S,T)=\langle p_1 p_2 \ldots p_L \rangle$, where L is the largest subset of words from S that found a partial match in T, and $p_i$ is a partial match of a word $s_i \in S$ to a word in T. A word $s_i$ in S is said to partially match a word $t_j$ in T if it shares a maximum length common prefix $p_i$ such that $$\frac{|p_i|}{\max\{|s_i|, |t_j|\}} \geq \tau.$$

If the threshold is =1.0, this reduces to the case of finding exact matches to words of S.

In various examples, the prefixes are chosen to correspond to the English grammar rules where many word forms of words share common prefixes. This allows modeling word variants such as regurgitated, regurgitating, and regurgitation as they all share a sufficiently long prefix 'regurgitat'. It can also model spelling errors, particularly those that are made in the later portion of a word.

Similar to the longest common subsequence matching problem, it can be shown that the longest common subfix algorithm also obeys the principle of optimality, allowing the best matching sequence to be computed using popular dynamic programming algorithms in time quadratic in the length of the sequences to be matched. For this, an array C[i,j] is kept to calculate the score of matching a fragment of S up to the i-th word and fragment of T up to the j-th word. The dynamic programming matrix is then updated according to the algorithm shown in Inset 1. Here $p_{max}(i,j)$ is the longest prefix of the strings $s_i, t_j$ and $\delta$ is a mismatch penalty, which controls the separation between matched words and prevents words that are too far apart in a sentence from being associated with the same vocabulary phrase, thus minimizing the effect of incorrect anaphora resolution in a sentence. Using this algorithm, a vocabulary phrase S is said to be detected in a sentence T if $$\frac{|LCF(S,T)|}{|S|} \geq \Gamma$$

for some threshold $\Gamma$. The choice of $\tau$ and $\Gamma$ affect precision and recall in matching and can be chosen to meet predetermined criteria for precision and recall based on an ROC curve analysis as is popular in information retrieval literature. Note that the normalization in the above equation is on the length of the vocabulary phrase and not the sentence allowing matches to be found in long sentences.

---

Inset 2

```
LCF(S,T);
C[i, 0] = 0, C[0, j] = 0, 0 ≤ i ≤ K, 0 ≤ j ≤ N
for (1≤ i ≤ K)
    for (1≤ j ≤ N)
    {
        ρ_ij = |p_max(i,j)| / max{|s_i|,|t_j|};
        If C[i-1,j-1] + ρ_ij > C[i-1,j] && C[i-1, j-1] + ρ_ij > C[i,j-1]
            C[i,j] = C[i-1,j-1] + ρ_ij;
        Else
        {
            If C[i-1,j] + ρ_ij > C[i,j-1]
                C[i,j] = C[i-1,j] – δ;
            Else
                C[i,j] = C[i,j-1] – δ;
        }
    }
```

---

Table 1 shows the results of applying the longest common subfix algorithm on a variety of sentences found in textual reports. From the first result in Table 1, it can be seen that the algorithm was able to spot the occurrence of both 'aortic sclerosis' and 'aortic stenosis' in the sentence, even though the words 'aortic' and 'stenosis' are separated by several words in between. Similarly, the vocabulary phrase 'left atrial dilatation' was matched to 'Left Atrium: Left atrial size is mildly dilated' even without deep understanding of the linguistic origins of the underlying words.

With the flexibility of matching in longest common subfix algorithm for tolerating word form and order variations within vocabulary phrases, the chance of false matches can increase. For example, a vocabulary phrase such as 'degenerative joint disease' may match a sentence 'Right hip degenerative disease' since 2 of the 3 long words in the vocabulary have an exact match in this case. The false matches can be mitigated by requiring that certain must-have prefixes be found in the sentences in order to initiate the longest common subfix matching. These must-have prefixes should be such that they are necessary and sufficient to locate the vocabulary phrase. As an example, suppose there were three vocabulary phrases: 'localized', 'local', 'locally', then their shortest prefixes that distinguish between them are 'locali', 'local', and 'locall' respectively.

Finding evidence for one of these prefixes is both necessary and sufficient to recognize their corresponding vocabulary phrase. By comparing words in the vocabulary phrases against common words in a large clinical word dictionary, such shortest discriminable prefixes can be computed for each word to become the must-have terms that give a very reliable indication of the vocabulary phrases and overcome some of the false positives that could occur due to inexact matching.

In various embodiment, an algorithm to automatically generate the must have terms for the vocabulary phrases is provided. In one example, using the same training collection of 1.2 million reports, all distinct words were extracted in all sentences of the reports to create an initial clinical word dictionary of over 65,502 words. To this, all prefixes of these words of length greater than 3 were added, and stop words were removed to generate a collection of over 1 million prefixes. If two words share a prefix, then this is recorded for the prefix by a Boolean flag indicating it is a shared prefix. Next, words are extracted from the vocabulary phrases in the vocabulary bank and it is shrunk to its smallest prefix that was not also shared with another word prefix in the word dictionary. This algorithm is summarized in Inset 3. Examples of prefix strings generated for sample vocabulary phrases in our dictionary are shown in Column 1 of Table 1. As can be seen, in each case, the must-have terms are fairly indicative of the vocabulary phrase so that if an exact match to these terms is found prior to initiating the inexact matching using the LCF algorithm, the false positive matches are virtually eliminated while still allowing for tolerance in word form variations.

Inset 3

```
findSmallestForm (word)
{
        found = false;
        i = word.length( );
        prefix = word;
        while (!found && i >= 3)
        {
            prefix = word.substring(0,i);
            if ((prefix not in wordMap) || (prefix not shared in
            wordMap))
            {
                i--; // continue shrinking
            }
            else
            {
                found = true;
                prefix = word.substring(0, i + 1);
            }
        }
        return prefix;
}
```

With enhanced vocabulary, the lexical matching of the concept extraction algorithm can detect the presence of concepts. In order to detect if these vocabulary phrases are occurring in a negated context, a negation detection algorithm is provided. In some embodiments, this algorithm does an independent analysis of the sentence to capture the local and global context. In particular, starting from a dependency parse tree of a sentence, a set of known typed dependency patterns developed by a universal dependency parser (e.g., the Stanford NLP parser) are used to search for negations and the scope of words spanned by a negation keyword. These negation patterns are shown in Table 2. To search for negations, the negation patterns are instantiated using common negation words combined with new negation terms mined from a large corpus of clinical reports.

The negation detector herein differs from alternative approaches to negation detection in several aspects. The negation detector herein does not require a targeted concept as input, but returns the scope of negation in a sentence in one shot, making it possible to parallelize concept extraction and negation detection on big data. In addition, it is able to capture long-distance negations within a dependency parse tree by recursively identifying negated words until the detected scope of negation converges, without limiting the diameter of the scope. Recursive detection relies on a rich list of negation cues, along with carefully curated rules covering the variety of dependencies.

In one example, 165 additional negation patterns were collected (e.g., 'no,x,detected') from the most frequent negation phrases found during vocabulary learning on the 1.2 million reports described earlier. The most informative word was then extracted from each pattern (negation cues, e.g., 'no' as in 'no,x,detected'), and identified a comprehensive list of grammatical relations/dependencies between a negation cue and a potentially negated word according to the typed dependencies as shown in Table 2. For certain types of negation cues, especially adjectives, their antonym (e.g., likely vs. unlikely) is also considered as a negation cue when co-occuring with a negation modifier.

The negation pattern detection algorithm iteratively identifies words within the scope of negation based on dependency parsing. Let S be the set of negated words. The algorithm starts by adding a collection of manually curated negation cues (e.g., 'no') into S, and then iteratively expand S through traversing the dependency parse tree of a sentence, until S becomes stable.

Figure 2:
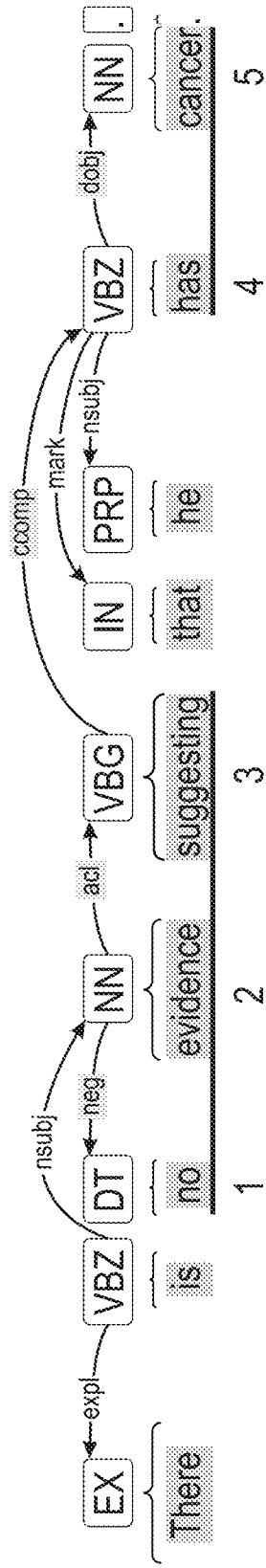
FIG. 2 illustrates an example of iteratively identifying words within the scope of negation according to embodiments of the present disclosure.

FIG. 2 illustrates the negation detection algorithm according to embodiments of the present disclosure. Based on the language analysis of the sentence and the negation pattern matches, the negation scope is listed as: 'evidence', 'suggesting', 'has', and 'cancer', and the target vocabulary phrase is identified as 'cancer'.

Combining the above language analysis with lexical concept extraction described above, the negation scope is used to filter positive and negative occurrences of concepts and make reference to context associations of negated vocabulary phrases.

TABLE 2

| Typed dependency | Examples | Negation cues |
| --- | --- | --- |
| Negation modifier | neg(*, not) | Not, no, n't, non, false |
| Prepositional modifier | prep_of(absence, *) | Absence, free, none, exception |
| Nominal subject | nsubj(normal, *) | Normal, exception, unremarkable, clear, non-restricted, absent, negative, questionable |

TABLE 2-continued

| Typed dependency | Examples | Negation cues |
|---|---|---|
|  | nsubj(present, *) && neg(present, not) | Present, positive, definitive, necessary |
| Object of a preposition | pobj(except, *) | Except, without |
| Direct object | dobj(deny, *) | Deny, defer, negate, refuse, resolve, rule, quit, exclude |
| Clausal complement with external subject | xcomp(unlikely, *) xcomp(likely, *) && neg(likely, not) | Unlikely, unable, impossible, untypical Likely, able, possible, typical |

TABLE 3

| | |
|---|---|
| FP | She has not used any anti retroviral therapy since then, because of pancytopenia and vomiting on DDI. |
| FP | The differential diagnosis includes, but is not limited to, sarcoma, spindle cell carcinomas (sarcomatoid carcinoma of the upper aerodigestive tract and anaplastic thyroid carcinoma), and malignant salivary gland neoplasms. |
| FP | There was no evidence of continued bleeding and her HCT remained stable around 30. |
| FN | She ruled out for myocardial infarction with 3 negative enzymes. |
| FN | On POD#9, the patient was afebrile, tolerating a regular diet, ambultating without difficulty and voiding spontaneously. |

In Table 3, examples of errors from the NegEx detector (FP for false positive, FN for false negative are shown).

The negation detection algorithm performs well on the NEGEX collections and even better on collections drawn from i2b2 data collections, one from the NegEx release that consists of 2376 targeted phrases (20.7% negated), and the other developed in house that consists of 1061 concepts in question (47.9% negated). Table 4 shows the precision, recall, and F-score comparison of NegEx and our iterative negation detection algorithm. On the NegEx data, both algorithms have comparable performance achieving 97% F-score. On in-house test data assembled from i2b2 reports, and focusing on linguistically complex sentences such as the one shown in table above, the algorithm performs significantly better, with 32% higher precision and 14% higher recall. Table 3 shows examples of sentences flagged by NEGEX that are correctly processed by our negation detection algorithm.

The majority of errors made by the algorithm are due to suboptimal output from dependency parsing. For instance, for the sentence 'She does not drink, use IV drugs or smoke', an unspecified relation between the words 'drink' and 'use' is returned by the parser, which ideally should be marked as a 'conjunction' relation instead. The negation detector that is entirely based on traversing parse trees fails in such cases. A potential solution would be to use a hybrid detector taking advantage of both regular expression matching and dependency parsing.

TABLE 4

| Data Collection | % negations | Algorithm | Precision | Recall | Fscore |
|---|---|---|---|---|---|
| NegEx Collection | 20.7% | NEGEX | 93% | 96% | 0.978 |
| NegEx Collection | 20.7% | Iterative Negex | 95% | 93% | 0.974 |
| In-house Collection | 47.9% | NEGEX | 65% | 74% | 0.68 |
| In-house Collection | 47.9% | Iterative Negex | 97% | 88% | 0.93 |

Table 4 illustrates the performance of the negation detector.

Figure 3:
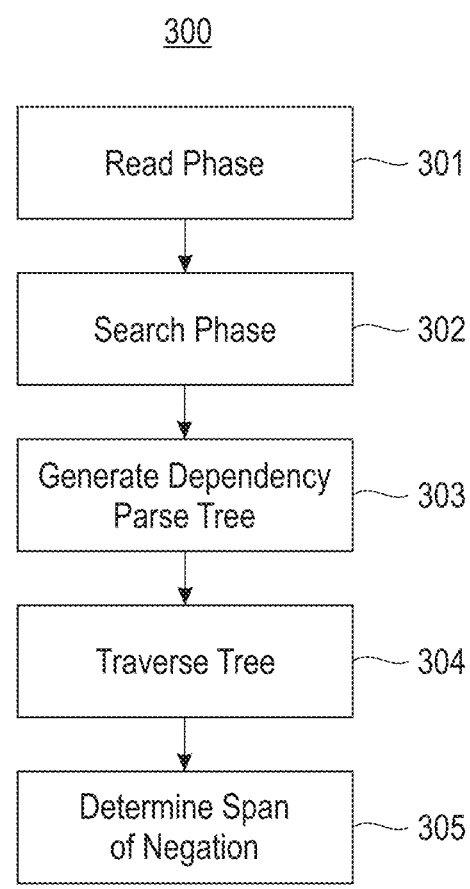
FIG. 3 illustrates a method of negation scope analysis according to embodiments of the present disclosure.

Referring now to FIG. 3, a method for negation detection according to embodiments of the present disclosure is illustrated. At 301, a phrase is read from a report collection. At 302, the phrase is searched for at least one of a predetermined set of negation keywords. At 303, generating a dependency parse tree of the phrase. At 304, the dependency parse tree is traversed starting with the at least one of the predetermined set of negation keywords. At 305, based on the traversal, a plurality of words of the phrase are determined that are spanned by the at least one of the predetermined set of negation keywords.

Although the string matching algorithm accounts for variational appearance of vocabulary phrases, finding matches for all possible vocabulary phrases in large report collections is still a computationally challenging problem. The algorithm described herein is quadratic in the number of words in each phrase to be matched. So, if there are 1 million words in a vocabulary, and 10 million reports in which the clinical concepts of the vocabulary to be found, then even assuming an average of 20 sentences per report, and 10 words per sentence, and 5 words per vocabulary phrase, there are $10^6*5*10*20*10*10^6=10^{16}$ positions to be searched for potential matches which could take months to search on current hardware. To address this problem, the present disclosure provides an indexing method that significantly reduces this search while still maintaining the requisite precision in matching.

Consider a report collection $D=\{D_1, D_2, \ldots D_M\}$ of size M. Let $T_{lk} \in D_l$ represent the k-th sentence belonging to the l-th report $D_l$, consisting of a sequence of words $T_{lk}=<t_{lk1} t_{lk2} \ldots t_{lkN_{lk}}>$ of length $N_{lk}$. Let the vocabulary bank be $S=\{S_1, S_2, \ldots S_V\}$ of size V and let each vocabulary phrase be described by its sequence of non-stop words $S_i=\{s_{i1}, s_{i2}, \ldots s_{iK_i}\}$ of length K. Using the must-have prefix terms, the vocabulary phrase can also be denoted by the sequence $S_i=\{w_{i1}, w_{i2}, \ldots w_{iK_i}\}$ where $w_{ij}$ is the must-have prefix of the word $s_{ij}$ which must be matched for the word $s_{ij}$ to be recognized in the sentence.

To allow indexing, the reports are pre-processed to extract all prefix strings of non-stop words and form a reverse index. In particular, some embodiments adopt the Lucene text search indexing mechanism, and create documents in the index as $p_m(t_{lkj})$: $=<t_{lkj}, T_{lk}, D_l>$ where $p_m(t_{lkj})$ is a prefix of length m for the j-th word $t_{lkj}$ in the k-th sentence $T_{lk}$ belonging to the l-th report $D_l$. Then starting from the must-have prefixes of each vocabulary phrase $S_i = \{w_{i1}, w_{i2}, \ldots w_{iK_i}\}$, all relevant reports $D_R \subseteq D$ can be found that are likely to contain a mention of the vocabulary concept $S_i$ as those reports for which the histogram of hits for the vocabulary phrase $S_i$ exceeds a threshold $\Gamma$:

$$H_d(S_i) = \frac{\sum_{j=1}^{K_i} h_d(S_{ij})}{K_i} > \Gamma, \text{ where}$$

$$h_d(s_{ij}) = \begin{cases} 1 & \text{if } \exists\, p_m(t_{lkj}) \text{ s.t. } w_{ij} = p_m(t_{lkj}) \\ 0 & \text{otherwise} \end{cases}.$$

In the above formula, the histogram counts what fraction of the must-have vocabulary words find an exact match in some single sentence within a report. Using platforms such as Lucene, the exact lookup may be automatically enabled by querying the index with the must-have terms of the given vocabulary phrase. In fact, using such a Lucene index, the most likely sentences can be determined for using the detailed LCF matching within the selected reports $D_R$ for the concept $S_i$ as those sentences $T_R = U_{l=1}^{|D_R|} T_l$ in which the must-have prefixes found a match, i.e., $T_{lk}$, s.t. $\exists t_{lkj} \in T_{lk} \wedge w_{ij} = p_m(t_{lkj})$. Using the same threshold $\Gamma$ as used in the LCF algorithm ensures that the subsequent LCF matching is bound by the same threshold.

In the above analysis, it is assumed that the number of reports and sentences is still far larger than the number of vocabulary phrases. Using the indexing the complexity of finding the clinical concepts reduces from exploring $\Sigma_{l=1}^{M} \Sigma_{k=1}^{M_l} N_{lk}$ matches to $\Sigma_{l=1}^{|T_R|} N_l$. In practice, since M=10 million, and $M_l$=100, and $|T_R|$=1000, there is a tremendous reduction of complexity by a factor of 6 (i.e. $10^6$) through such indexing.

Figure 4:
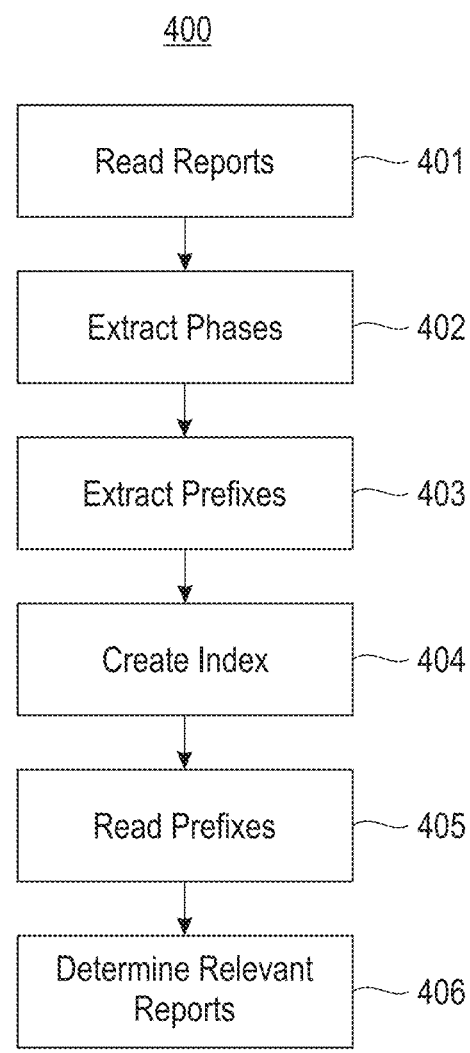
FIG. 4 illustrates a method of concept extraction according to embodiments of the present disclosure.

Referring to FIG. 4, a method of concept extraction is illustrated according to embodiments of the present disclosure. At 401, a plurality of reports is read from a report collection. At 402, each of the plurality of reports is divided into constituent phrases. At 403, a first plurality of prefixes is extracted from the constituent phrases of the plurality of reports. At 404, an index is created based on the first plurality of prefixes. At 405, a second plurality of prefixes is read. The second plurality of prefixes corresponds to a clinical concept. At 406, from the index, a subset of the plurality of reports is determined that are relevant to the clinical concept.

Figure 5:
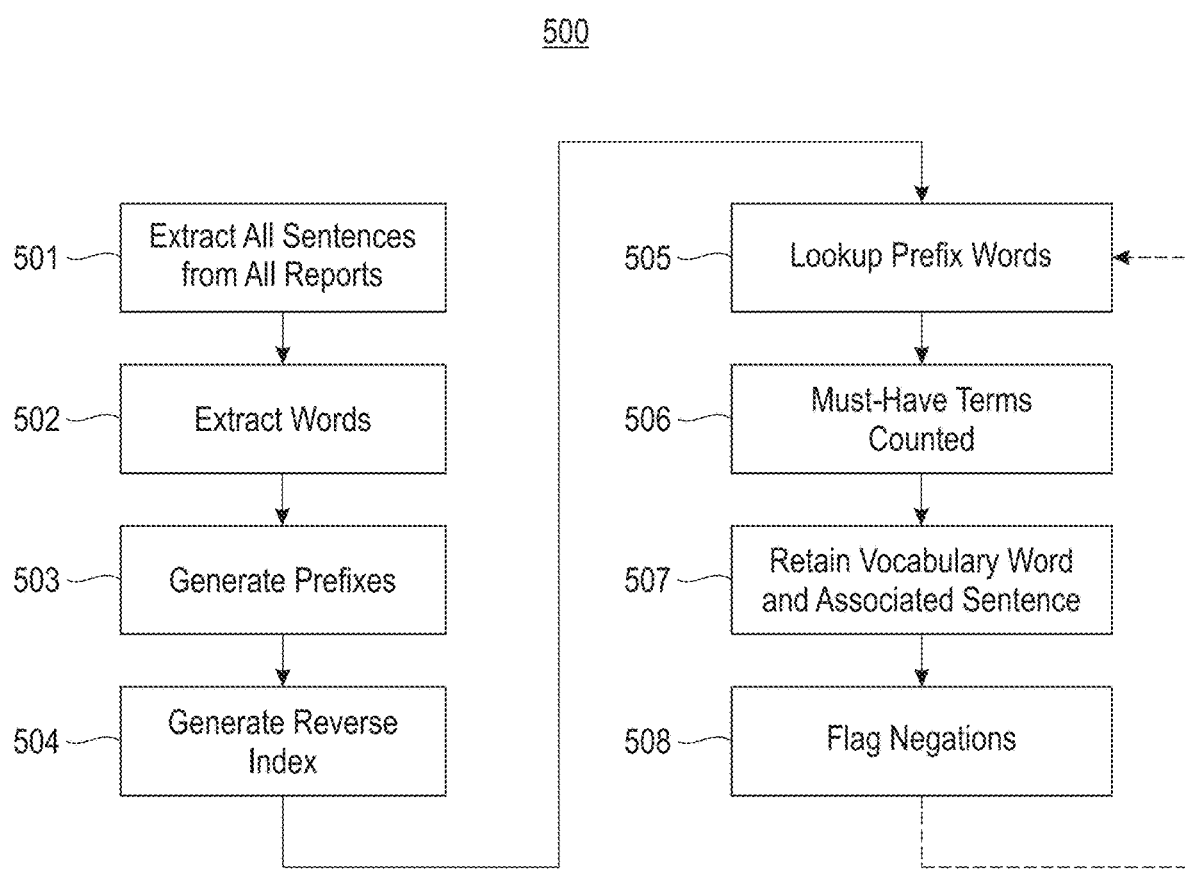
FIG. 5 illustrates an end to end concept extraction method according to embodiments of the present disclosure.

Referring to FIG. 5, an end to end concept extraction method integrating the above components is illustrated according to embodiments of the present disclosure.

At 501, given a collection of reports D={$D_1, D_2, \ldots D_M$} preprocess, extract all sentences from all reports. To account for scrolling, extra carriage returns due to formatting of textual reports (particularly when they are part of HL7 messages), group multiple lines of text in reports that are separated by carriage returns, hyphens, etc. to form candidate long sentences within which we search for conventional sentence separators.

At 502, words are extracted from sentences ignoring stop words, numbers, and other special character words. A language analysis is performed of the sentences, producing dependency parse trees.

At 503, all prefixes of at least length 3 are generated. In some embodiments, the stop words are removed again from the prefix words.

At 504, a reverse index of words, sentences, and reports is generated from the prefix words.

At 505, for each must-have term $w_{ij}$ in the vocabulary phrase $S_i$, matching prefix words are looked up in the index and their associated sentences and reports per match are determined. In some embodiments, the index is based on Lucene.

At 506, the fraction of must-have terms are counted that find a match per report in some sentence using the above formula. The result is normalized to get a histogram.

At 507, the vocabulary word and the associated sentences are retained in the reports index for detailed LCF matching.

At 508, negations are flagged based on negation cues and dependency parsing as described above.

Steps 505-508 are repeated for all words in the vocabulary to find all clinical concepts in all textual reports.

Results of evaluation of the clinical concept extraction algorithm and the negated context detection on several datasets are provided below.

In a first example, a set of 179 clinical reports from the i2b2 dataset of 2010 concept annotation challenge was tested. Ground truth labeling of problems or diseases was available for 91 reports. The clinical concepts detected by our algorithm were filtered for problems using the same UMLS categories as used by the ground truth labeling algorithm ('T020', 'T190', 'T049', 'T019', 'T047', 'T037', 'T048', 'T191', 'T046', 'T184', 'T005') as concept extractor finds concepts by approximate matching, the comparison with the ground truth labeled phrases was done by matching with the phrase in the sentence spanned by the LCS match that contained the vocabulary concept. The extent of overlap between the indicated matching phrase and ground truth labeled phrase was used to determine a match. Precision was defined as the fraction of matching phrases indicated in the ground truth while recall was defined as the fraction of ground truth phrases that found a match with the indicated phrases spanning a vocabulary by the LCS matching algorithm. Performance was compared to the popular CTakes algorithm on this dataset, and the results are shown in Table 5 (i2b2 collection). As can be seen, algorithm according to the present disclosure are significantly above alternatives for problem identification.

TABLE 5

| | Precision | Recall |
|---|---|---|
| I2B2 Collection | | |
| cTakes | 46.7% | 79.6% |
| LCF | 72.6% | 90.4% |
| Echocardiogram Collection | | |
| LanguageWare | 80.1% | 48.1% |
| cTakes | 34.0% | 59.6% |
| LCF | 78.2% | 79.3% |

TABLE 6

| | Collection Size Million Report Collection | Accuracy |
|---|---|---|
| Diagnosis | 669,832 | 96% |
| Measurements | 2,976,490 | 94.8% |

TABLE 6-continued

|  | Collection Size Million Report Collection | Accuracy |
| --- | --- | --- |
| Drugs | 1729 | 97.4% |
| Symptoms | 8,141,585 | 93.6% |

In another example, to test the generalizability of these approaches to other report collections, 753 echocardiogram reports were selected from a hospital partner and divided among 5 experts to spot disease mentions in the reports. In each case, the experts were asked to highlight the sentences containing the disease mentions. In cases where more than one disease mention occurred in a sentence, the sentence was repeated in the ground truth table, once for each disease mention. The experts did not label the disease but only pointed to the sentence containing the disease mention. For this experiment, the concept extraction algorithm was evaluated for disease mentions and compared to cTakes and LanguageWare. Both cTakes and LanguageWare use exact matching of phrases, so the difference in performance would illustrate the effect of the choice of the algorithm. Since neither algorithm exposed their vocabulary, the algorithms were run on the same 753 report dataset and allowed to use their respective vocabularies. The results of the comparison are shown in Table 5 (Echocardiogram collection). As can be seen, the present methods have the best recall while sacrificing only a small amount on the precision.

In another example, accuracy of the concept extractor was tested on a very large collection of over 12.9 million textual reports depicting over 200 different types of reports including radiology, pathology, transcription, etc. collected from over 800,000 patients. The total number of concepts detected in the unstructured reports and their accuracy is shown in Table 6 (Million report collection). The highest number of detected concepts were for symptoms as they are least often described in structured reporting but found within unstructured reports. Medication concepts were the lowest since they are mostly found in the structured sections of HL7 messaging from pharmacy systems. In general, on the average 60% more data were added to a patient profile through the unstructured mining of clinical concepts.

In the present disclosure, the problem of approximately matching a very large number of concepts in a large collection of textual reports in a large electronic health record system is addresses. The present algorithms outperform alternatives in concept extraction and is the largest tested algorithm to date. Issues of scalability and time performance have been addressed by the indexing of reports prior to matching. The longest common subfix matching is a generalized algorithm that can replace alternative string matching algorithms in many lookup tasks besides clinical concept extraction such as in dictionary lookups, and mapping.

Figure 6:
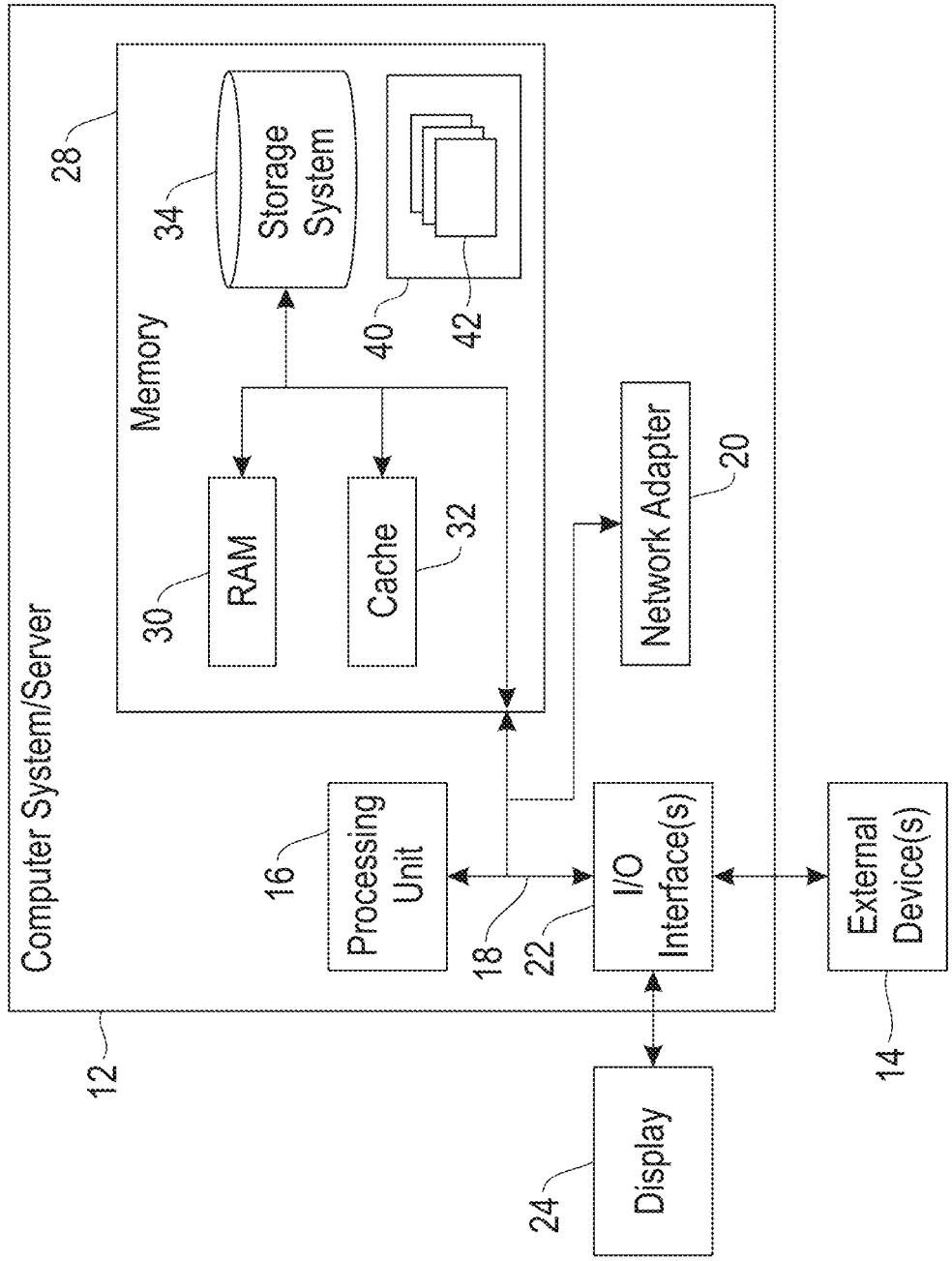
FIG. 6 depicts a computing node according to an embodiment of the present invention.

Referring now to FIG. 6, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 6, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   reading a phrase from a report collection;
   searching within the phrase for at least one negation keyword of a predetermined set of negation keywords;
   generating a dependency parse tree of the phrase, the dependency parse tree comprising the at least one negation keyword connected to a dependency chain comprising a plurality of words depending from the at least one negation keyword, wherein each of the plurality of words within the dependency chain comprises a directional dependency to another one of the plurality of words;
   starting with the at least one negation keyword, traversing the dependency chain by iteratively identifying words within a scope of negation and ceasing traversing when the scope of negation becomes stable; and
   based on the traversal of the dependency chain, determining a noun phrase within the plurality of words spanned by the at least one negation keyword.

2. The method of claim 1, wherein traversing the dependency chain comprises adding to the predetermined set of negation keywords at least one additional negation keyword.

3. The method of claim 1, wherein searching within the phrase comprises applying one or more regular expressions to the phrase.

4. The method of claim 1, wherein the predetermined set of negation keywords is generated by vocabulary learning.

5. The method of claim 1, wherein the predetermined set of negation keywords comprises at least one term and its antonym.

6. A computer program product for negation detection, the computer program product comprising a computer readable storage medium having program instructions embodied therewith, the program instructions executable by a processor to cause the processor to perform a method comprising:
   reading a phrase from a medical report collection;
   searching within the phrase for at least one negation keyword of a predetermined set of negation keywords;
   generating a dependency parse tree of the phrase, the dependency parse tree comprising the at least one negation keyword connected to a dependency chain comprising a plurality of words depending from the at least one negation keyword, wherein each of the plurality of words within the dependency chain comprises a directional dependency to another one of the plurality of words;
   starting with the at least one negation keyword, traversing the dependency chain by iteratively identifying words within a scope of negation and ceasing traversing when the scope of negation becomes stable; and
   based on the traversal of the dependency chain, determining a noun phrase within the plurality of words spanned by the at least one negation keyword.

7. The computer program product of claim 6, wherein traversing the dependency chain comprises adding to the predetermined set of negation keywords at least one additional negation keyword.

8. The computer program product of claim 6, wherein searching within the phrase comprises applying one or more regular expressions to the phrase.

9. The computer program product of claim 6, wherein the predetermined set of negation keywords is generated by vocabulary learning.

10. The computer program product of claim 6, wherein the predetermined set of negation keywords comprises at least one term and its antonym.

11. A system comprising:
    a data store comprising a medical report collection;
    a computing node comprising a computer readable storage medium having program instructions embodied therewith, the program instructions executable by a processor of the computing node to cause the processor to perform a method comprising:
    reading a phrase from the medical report collection;
    searching within the phrase for at least one negation keyword of a predetermined set of negation keywords;
    generating a dependency parse tree of the phrase, the dependency parse tree comprising the at least one negation keyword connected to a dependency chain extending from the at least one negation keyword, wherein each of the plurality of words within the dependency chain comprises a directional dependency to another one of the plurality of words;
    starting with the at least one negation keyword, traversing the dependency chain by iteratively identifying words within a scope of negation and ceasing traversing when the scope of negation becomes stable;
    based on the traversal of the dependency chain, determining a noun phrase within the plurality of words spanned by the at least one negation keyword.

12. The system of claim 11, wherein traversing the dependency chain comprises adding to the predetermined set of negation keywords at least one additional negation keyword.

13. The system of claim 11, wherein searching within the phrase comprises applying one or more regular expressions to the phrase.

14. The system of claim 11, wherein the predetermined set of negation keywords is generated by vocabulary learning.

\* \* \* \* \*